United States Patent [19]

Eisert

[11] 4,110,043

[45] Aug. 29, 1978

[54] APPARATUS FOR COUNTING AND CLASSIFYING PARTICLES

[75] Inventor: Wofgang Günter Eisert, Hannover, Fed. Germany

[73] Assignee: Gesellschaft fur Strahlen- und Umweltforschung mbH, Munchen, Neuherberg, Germany

[21] Appl. No.: 726,275

[22] Filed: Sep. 24, 1976

[30] Foreign Application Priority Data

Sep. 27, 1975 [DE] Fed. Rep. of Germany ....... 2543310

[51] Int. Cl.² .................... G01N 15/02; G01D 21/04; G01N 21/00
[52] U.S. Cl. ............................. 356/102; 250/222 PC; 356/103
[58] Field of Search .............................. 356/102, 103; 250/222 PC

[56] References Cited

U.S. PATENT DOCUMENTS

| 3,661,460 | 5/1972 | Elking | 250/222 PC |
| 3,662,176 | 5/1972 | Kamentsky | 250/222 PC |
| 3,790,760 | 2/1974 | Stiller | 356/102 |
| 3,871,770 | 3/1975 | Behrens | 356/103 |
| 3,984,307 | 10/1976 | Kamentsky | 250/222 PC |

*Primary Examiner*—Samuel W. Engle
*Assistant Examiner*—Donald P. Walsh
*Attorney, Agent, or Firm*—Spencer & Kaye

[57] ABSTRACT

Apparatus for counting and classifying particles and including a laser for producing a laser beam, a flow nozzle for hydrodynamically focussing a stream of such particles and directing the focussed stream to intersect the laser beam, a focussing system causing the laser beam to have a diameter which, at the point of intersection with the particle stream, is no greater than the width of the particles, and a detector disposed to receive the laser radiation transmitted by the particles as they pass through the laser beam.

7 Claims, 7 Drawing Figures

APPARATUS FOR COUNTING AND CLASSIFYING PARTICLES

BACKGROUND OF THE INVENTION

The present invention relates to apparatus for counting and classifying particles by directing a laser beam toward the particles and sensing the radiation by means of a detector.

For various purposes, it is necessary to count and record the size distribution of cells and particles with simultaneous classification according to certain cell characteristics. However, numerous problems have been encountered in procedures thus far devised for performing these operations.

One known process based on the Coulter principle provides for electronic measurement of the cell volume on the basis of changes in resistance of an electrolyte liquid during passage of the cells through an opening in a partition.

It has also been proposed to employ optical flow-through methods which entail fluorescence measurements with colored particles and differentiation according to the intensity of the fluorescence, or scattered light measurements in which a coherent light source is scattered at particles, or measurements of the absorption of the entire cell on object carriers. In all these optical processes the measuring volume is greater, however, than the cell or particle to be measured, respectively.

In measurement procedures according to the Coulter principle, the measured value depends on the geometry of the measuring opening in the partition and on the location of the path of travel of the particles through the measuring opening. No information other than cell volume can be obtained about the particles. Moreover, there exists a danger of the measuring opening becoming clogged and the maximum cell diameter is limited to 50% of the measuring opening. The result is a low counting rate which is still dependent on particle size.

Fluorescence measurements have the drawback that the measured value is dependent on the coloration processes, i.e., different measuring series cannot be directly compared with one another and fluorescence colorations of special cell characteristics can often not be produced at all. In the case of scattered light measurements it is necessary, in order to record a size distribution, to simultaneously effect measurements at various spatial angles. This has the result that only size distributions up to a maximum of about 10μ can be derived from scatter data. In the practice of both of these measuring methods, the particles are present in suspension and the optical quality of the suspension stream is also not optimally adapted to the index of refraction of the cells.

Absorption measurements have previously been successful only when the measuring field is larger than the cell cross section. The cells are here applied to object carriers, and this results in low counting and analysis speeds since the object carrier must, inter alia, be moved mechanically.

SUMMARY OF THE INVENTION

It is an object of the present invention to eliminate, or substantially reduce, the problems existing in known procedures of the type discussed above.

A more specific object of the invention is to determine the size distribution of cells or particles by an absorption procedure, for example for algae and pollen without coloration, tetrahymena pyriformis and blood cells or blood clots possibly with coloration and to permit distinction between live and dead cells of the same size by means of specific coloration.

According to the invention, the derivation of measured values is achieved by an adaptation of the index of refraction of the flow system for optimum resolution of a microscope, while determination of the length of the cell is achieved by pulse shape analysis, and cell content concentration is determined from the amplitude of the absorption pulse and from the combined measurement of two synergistic parameters by evaluation of the pulse integral.

These and other objects and capabilities are achieved, according to the invention, in apparatus for counting and classifying particles and including a laser for producing a laser beam and a laser radiation detector, by the provision of a flow nozzle for hydrodynamically focussing a stream of such particles and directing the focussed stream to intersect the laser beam, by causing the laser to impart to the laser beam a diameter which, at the point of intersection with the particle stream, is no greater than the width of the particles, and by disposing the detector to receive the laser radiation transmitted by the particles as they pass through the laser beam.

According to one preferred embodiment of the invention, the flow nozzle is disposed in a jacket pipe which conducts an entraining stream that entrains the thin particle stream. Furthermore, the jacket pipe may be designed, at least in the region of the flow nozzle, to be defined by two mutually parallel planar surfaces each having an aperture closed by a transparent planar disc through which the laser beam enters and exits.

In a preferred embodiment of the invention, the flow nozzle is fastened to the jacket pipe, an inlet is provided in the jacket pipe for a fluid producing the entraining stream, a common outlet is provided for the entraining stream, the particles and their carrier fluid, and a subatmospheric pressure is established at the jacket pipe outlet to suck out or press the fluids.

In further accordance with a preferred embodiment of the apparatus according to the invention, the laser beam impinges on the disc of the upper opening at right angles to the disc surface and is focussed within the thin particle stream, and the flow direction of the thin stream and the axis of the incident beam are also perpendicular to one another.

According to another advantageous embodiment of the apparatus according to the invention, the flow nozzle ends in a capillary nozzle and has a wider portion upstream of the capillary nozzle, the particles are mixed into the carrier fluid in the wider portion of the flow nozzle, and in the capillary tube the particles are oriented toward the direction of the thin stream.

According to the preferred embodiment of the invention, the detector detects the pulse shape to permit indication of the length of the particles, detects the absorption pulse amplitude to permit indication of the concentration of the substance constituting the particles, and produces a representation of the pulse integral.

As a result, the present invention makes it possible, in a flow-through process with hydrodynamic focussing, to have the particles or cells, respectively, pass through the focal point of a laser beam, the latter always being smaller than the region, or area, to be measured. The cells are individually aligned along a thin stream. The particle stream flow speed can advantageously be regulated, by means of a subatmospheric pressure system, to attain a value of more than 5 m/sec without any turbulence being produced.

The additional entraining stream permits adaptation of the index of refraction of the nozzle stream to planar glass surfaces so that the laser beam can be focussed to focal point diameters of about $1\mu$ in the particle stream. The maximum permissible cell diameter depends merely on the opening of the flow nozzle, and can possibly be more than $500\mu$. The minimum cell diameter that can be resolved depends on the diameter of the laser beam focal point, which theoretically is $1\mu$ and in practice is $3\mu$.

When the speed of the particle stream is constant, the passage time of the cells, which are always oriented to have their longitudinal axis in the direction of flow, is proportional to the length of the cells. Uncolored cells, due to their compartmentalized cell structure with different refraction indices, also show losses of transmitted light due to scattering. Absorption is therefore detected, according to the present invention, over a narrow spatial angle of 1° to 2° so as to eliminate the influence of the small angle of forward scattering. The width of an absorption pulse, measured between the half-amplitude points of the leading and trailing pulse edges, is thus a measure for the length of a cell. When special cell content substances are colored, the amplitude of the absorption pulse is a measure for the concentration of the colored substance in the cell strip under observation. If both parameters, amplitude and width of the absorption pulse, are directly proportional to a particular cell characteristic, the present invention provides that evaluation of the integrals of the absorption pulses will even more clearly show existing differences.

For each of the three measured values: pulse amplitude; half-amplitude pulse width value; and pulse integral, a known electronic system produces a rectangular pulse with constant pulse shape and an amplitude which is proportional to the measured value. The different pulse amplitude values are recorded in a multichannel analyzer to form a histogram.

A particular advantage of the present invention is that a size analysis is possible also for untreated cells and particles, i.e. no coloration is necessary. As is known, measured values may generally be changed significantly by a coloration process. Thus, for example, an aggregation of cells may come apart. A further size range can be detected without changing the flow system. Moreover, coloration produces additional information and the speed of the analysis is high. Flow speeds of more than 5 m/sec are possible. The processing speed is furthermore dependent only on the capabilities of the series-connected multichannel analyzer. When a distribution curve is measured, the greater part of the values can be electronically cut out. The recording speed of the curve values can be adapted to the mulitchannel analyzer. Thus, recording speeds of more than 200,000 samples/sec can be obtained for a total distribution.

DESCRIPTION OF THE PREFERRED EMBODIMENTS

It has been found that when cells of nonspherical shape are distributed in the laminar flow stream of a hydrodynamically focussed system, their major axes are oriented in the direction of flow. Thus mammalian erythrocytes are reshaped in such a stream to ellipsoidal bodies. The ratio of the ellipsoid axes varies from 4:1:1 to 2:1:1 and depends on the composition of the suspension medium.

If there is produced a thin stream of cells whose major axes are oriented perpendicular to the optical axis and which pass through the focal point of a laser beam, the absorption occurring in a disc-shaped section of the cell can be detected. The attenuation or extinction of light in accordance with Lambert's law is not the only reason for losses of incident light. Cell components also scatter the light. These so-called nonspecific losses lead to a detectable absorption signal even if the cell is not colored.

When certain conditions are met, the half-amplitude width of the detected absorption pulses is proportional to the length of the cells or particles. These conditions are that: the maximum diameter of the light beam through which the cells pass is at least somewhat smaller than the minimum width of the cells; the speed of the particle stream is kept constant during the measuring period; and any lateral movement of the cell in the plane perpendicular to the flow direction is no more than one-half the cell diameter.

The cell length measurement can be combined with a measurement of absorption over the length of the cell so that the integral of the absorption pulse is obtained. Cell lengths of the same size distribution but with different colorations can also be determined in this way.

Figure 1:
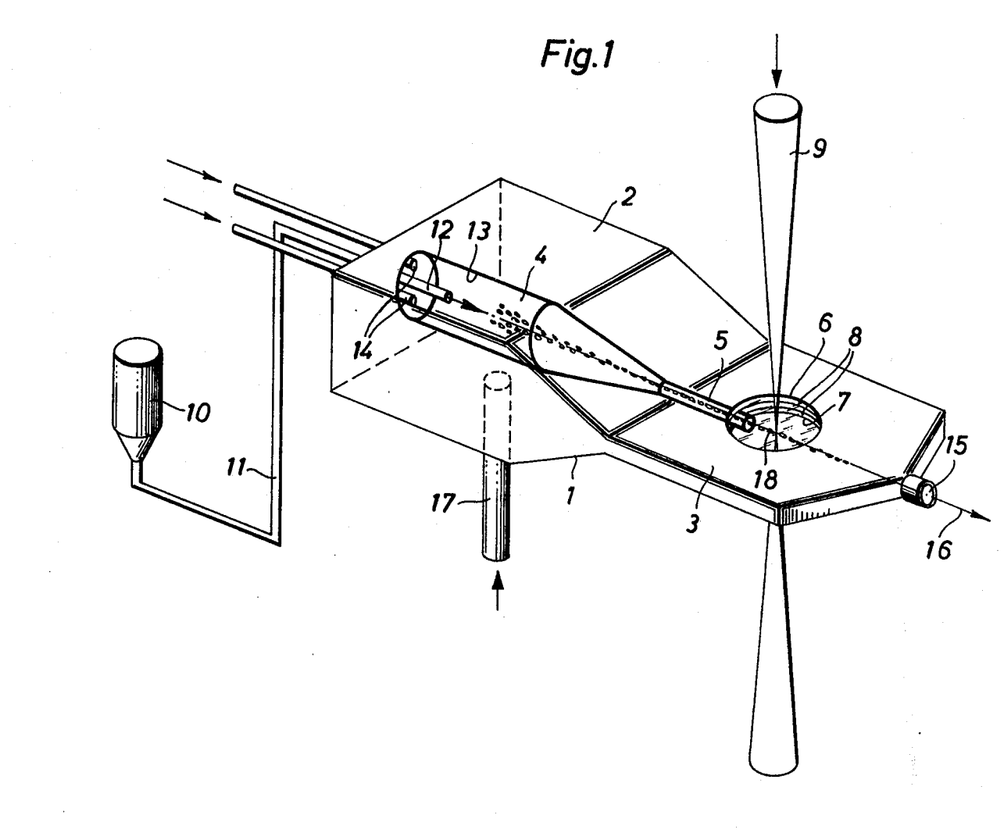
FIG. 1 is a perspective view of the central components of a preferred embodiment of the apparatus according to the invention. Portions of member 2 are shown as being transparent to permit illustration of the components therewithin.

FIG. 1 shows a flow system with which such measurements can be made. This system includes a jacket pipe 1 with a widened portion 2 and a thin portion 3, both of rectangular cross section. The transition between portions 2 and 3 is tapered and has a wedge shape. Within the jacket pipe 1 there is disposed a flow nozzle 4 which is tapered and ends in a capillary nozzle 5 of reduced diameter. The outlet end, or tip, of nozzle 5 is located in the region of two openings 6 and 7 each formed in a respective one of the large flat walls 3 of jacket pipe 1. The two openings 6 and 7 are closed by respective planar transparent discs 8 which are parallel to one another. Discs 8 are also disposed vertically on top of one another so that a laser beam 9 can pass through them.

A sample of cells in suspension is provided in a sample container 10 and is injected into the interior 13 of the flow nozzle 4 via a line 11 and an entrance nozzle 12. Two nozzles 14 through which can be introduced water or a buffer liquid to serve as a first entraining fluid also open into the interior 13 of flow nozzle 4.

The entrance nozzle 12, capillary nozzle 5 and outlet line 15 from the thin portion 3 of jacket pipe 1 are disposed on a common axis 16. A second entraining fluid is introduced into the widened portion 2 of the jacket pipe 1 via an inlet tube 17. Entrance nozzle 12 has, in a preferred embodiment, an inner diameter of 0.4 mm and the sample suspension introduced via nozzle 12 into nozzle 4 there forms a laminar flow with the aid of the first entraining fluid introduced through lines 14. If the pressure of the fluid introduced via lines 14 is somewhat higher than the entrance pressure of the sample fluid, an almost horizontal tapering of the stream is produced at the outlet of capillary nozzle 5. A typical pressure difference is in the range of 5 to 10 mm of water. Hydrodynamic focussing is realized by the special design of the flow nozzle 4 and capillary nozzle 5.

The second entraining stream introduced via line 17 surrounds this first mixture of sample and first entraining fluid from capillary nozzle 5 and produces a laminar flow within thin portion 3 of jacket pipe 1. Moreover, the sample stream or the thin stream and the entraining stream have the same optical index of refraction and therefore the optical fluid system is adapted to one another.

The inner diameter of the outlet end of capillary nozzle 5 can be 0.3 mm, for example, and can produce a sample stream diameter of $4\mu$. This is avaiable by making use of the principle of the hydrodynamic focussing and by an equivalent design of the inlet and outlet diameters of the tube 13 in relation to the inlet diameter of tube 12 (P. J. Crosland-Taylor, Nature 4340, 37(1953)).

Thus the minimum diameter for correct focussing of laser beam 9 is determined.

The limitation on the maximum diameter of the cells is determined by the inner diameter of capillary nozzle 5 and a nozzle of larger diameter can be provided to permit measurements to be performed on larger cells. The thin stream 18 traveling along axis 16 and including sample particles and the first entraining fluid is stable over a distance of a few millimeters. The axis of laser beam 9, as well as the axes of the incident light and of the transmitted light, are perpendicular to axis 16.

Figure 2:
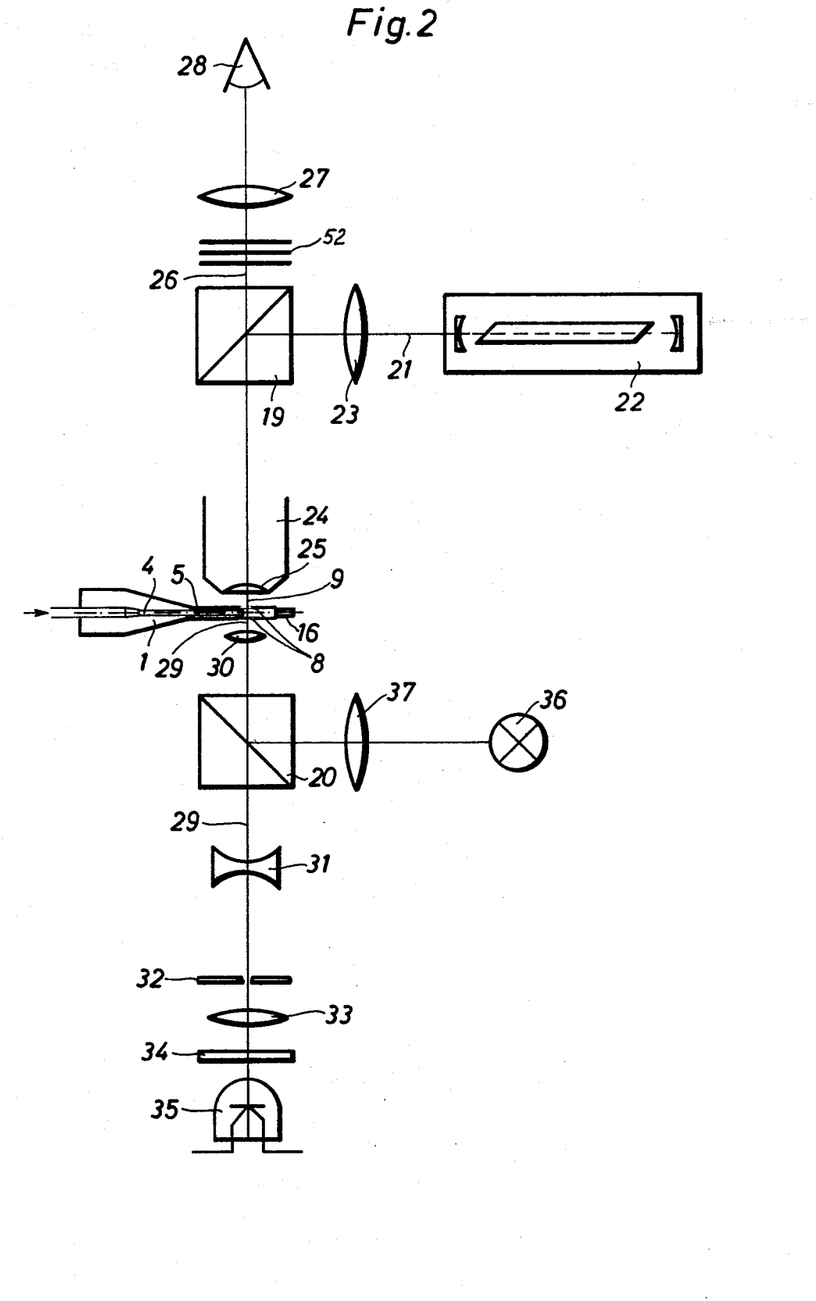
FIG. 2 is a simplified pictorial view of an optical measuring device containing the preferred embodiment of apparatus according to the invention.

The optical arrangement to effect measurements is shown schematically in FIG. 2 and includes two beam dividers 19 and 20 to permit optical control of proper beam alignment, as well as a 1 mW He-Ne laser 22 producing a laser beam 21. Beam 21 is directed through a correction lens 23 which is set to focus the laser beam 21 in the image plane of a microscope 24. The microscope utilizes an objective 25 producing a 40 × magnification.

The microscope includes an eyepiece 27 for permitting the eye 28 of an observer to view the point of intersection between beam 21 and stream axis 16. One portion 26 of beam 21 passes through eyepiece 27. For protection of the eye, a filter arrangement 52 is disposed between eyepiece 27 and beam divider 19 which includes a combination of three laser filters with absorption maxima near 6238Å. The minimum diameter of the focussed laser beam 9 leaving microscope 24 resulting from this optical arrangement is less than $1\mu$. Laser beam 9 is here focussed onto axis 16 which is the axis of the schematically illustrated jacket pipe 1 with flow nozzle 4 and capillary nozzle 5.

The laser beam 29 leaving jacket pipe 1, or its planar aperture discs 8, passes through a lens 30 and impinges as a collimated beam on beam divider 20. In order to eliminate errors in the scattered light measurements, only a cone of the laser beam 29 with an aperture angle of 2° is analyzed. In order to be able to do this, it passes through a double-concave lens 31 having focal lengths of $-12.5$ mm and an iris aperture 32. The beam portion passing through iris aperture 32 is recollimated by a lens 33 and passes through an interference filter 34 which permits measurements in illuminated environment. Thereafter, laser beam 29 impinges on a phototransistor 35 which is connected with a compensation unit (not shown) having a time constant of 0.2 $\mu$sec. The apparatus further includes an illumination lamp 36 and a further correction lens 37 providing a light beam which illuminates the object plane and for purposes of alignment. The filter 34 is commercial avaiable from Schott and Gen., Mainz, W-Germany, with the filter-type PJL 1 for the laser wavelength of 632 nm.

Figure 3:
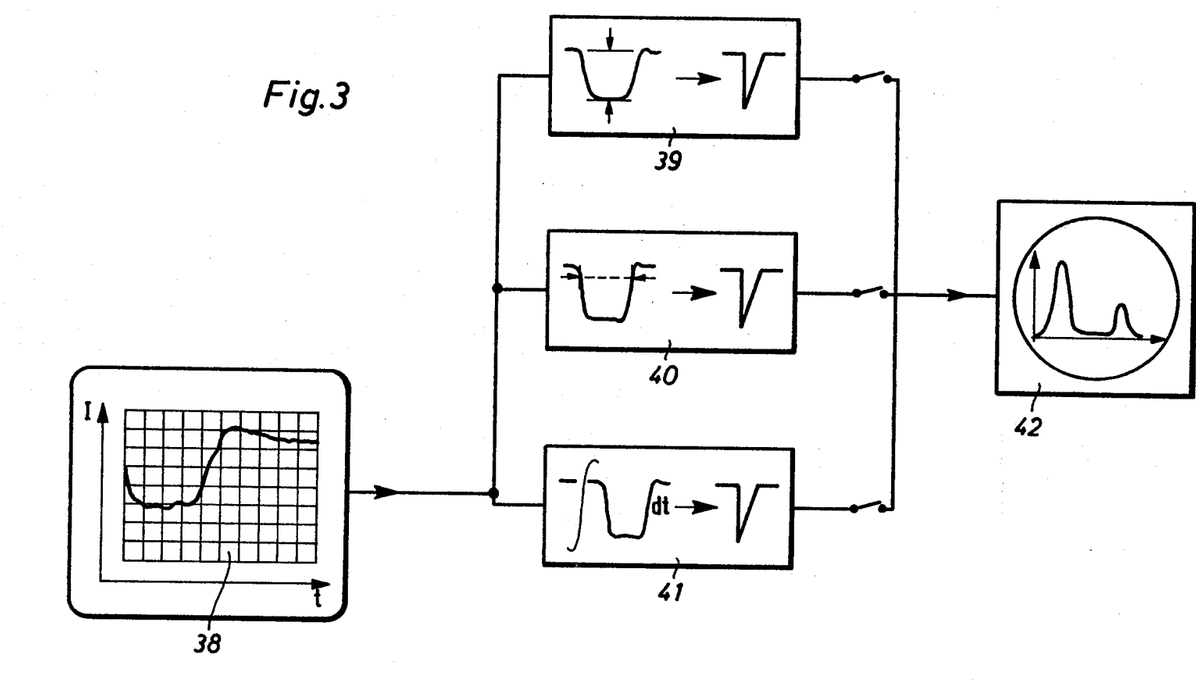
FIG. 3 is a simplified schematic diagram of a signal processing arrangement according to the invention.

FIG. 3 is a schematic diagram of one suitable signal processing unit. On the screen 38, for example, of an oscillograph with intensity and time axes, there is displayed a typical absorption signal which is produced by the absorption of laser light by the particles. Three simple analog computers 39, 40 and 41 of known design serve as an interface circuit between the vertical deflection signal to the oscilloscope and a multichannel analyzer 42, also of known design. This analyzer displays the distribution of the desired parameters.

Each analog computer 39 to 41 furnishes a pulse of constant shape derived from the original pulse amplitude, the pulse width and the pulse time integral, respectively, as shown schematically in the drawing. The amplitude of the constant shape pulse may be made proportional, in each respective analog computer, to the amplitude, the width, or the time integral, respectively, of the original pulse. For pulses with long half-amplitude widths and different shapes, the pulses must be reshaped with respect to pulse amplitude. These are requirements of the multichannel analyzer 42.

By employing the flow system shown in FIG. 1 and the analog computers shown in FIG. 3, it becomes possible to achieve pulse rates of more than 200,000 pulses/sec. This pulse rate is limited only by the conversion rate and the storage capacity of the multichannel analyzer 42.

The system can be used for measurements of, for example, tetrahymena pyriformis, red blood cells and blood clots. The size, for example, of the tetrahymena is related to the protein mass in the cells. Thus the length of the ellipsoidal particles provides information as to the protein content of the cells.

The results of various measuring operations effected with the apparatus of FIGS. 1 and 2 are illustrated in FIGS. 4–7 each of which is a diagram whose abscissa represents the channel numbers NO, of the multichannel analyzer 42 and whose ordinate represents the number, N, of pulses, or particles, whose value falls within a respective channel.

Figure 4:
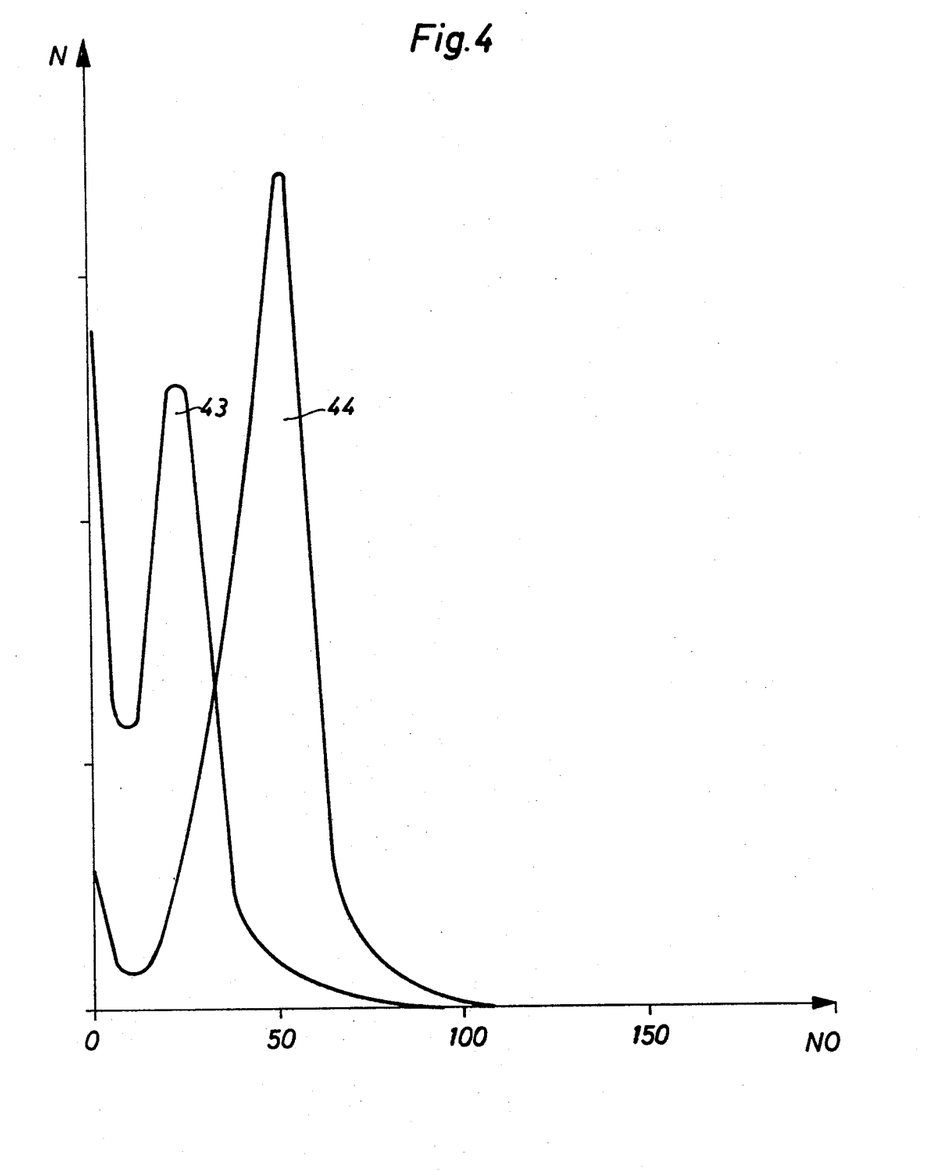
FIG. 4 is a diagram illustrating the measuring result produced by apparatus according to the invention for uncolored tetrahymena pyriformis.
Figure 5:
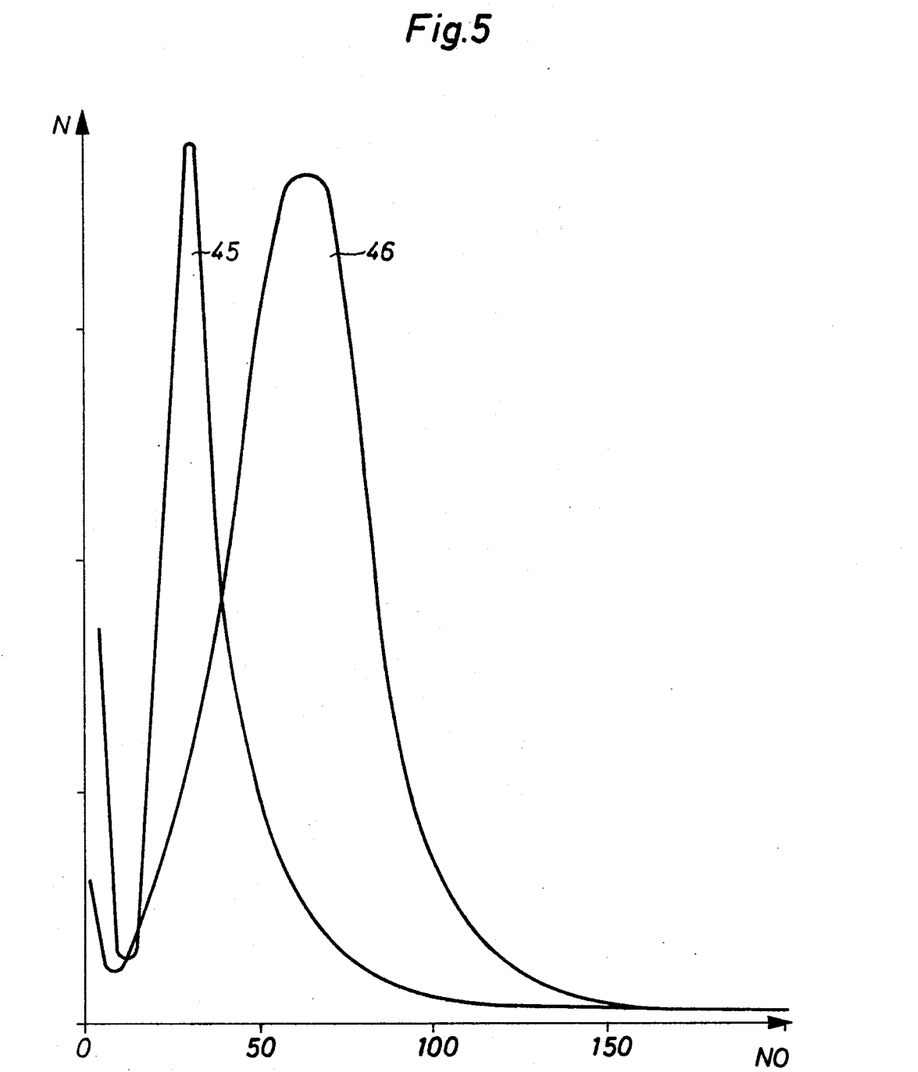
FIG. 5 is a diagram similar to that of FIG. 4 showing the measuring result for colored tetrahymena pyriformis.

FIG. 4 shows one exemplary measuring result for cell size distribution of uncolored tetrahymena pyriformis L. Curve 43 shows a distribution of particles of a nominal size of $40\mu$ and curve 44 is for particles of a nominal size of $80\mu$.

FIG. 5 again shows a size distribution of tetrahymena pyriformis L, curve 45 relating to a size of 40μ and curve 46 to a size of 70μ. However, in this case the particles were colored with naphthol-blue-black.

Figure 6:
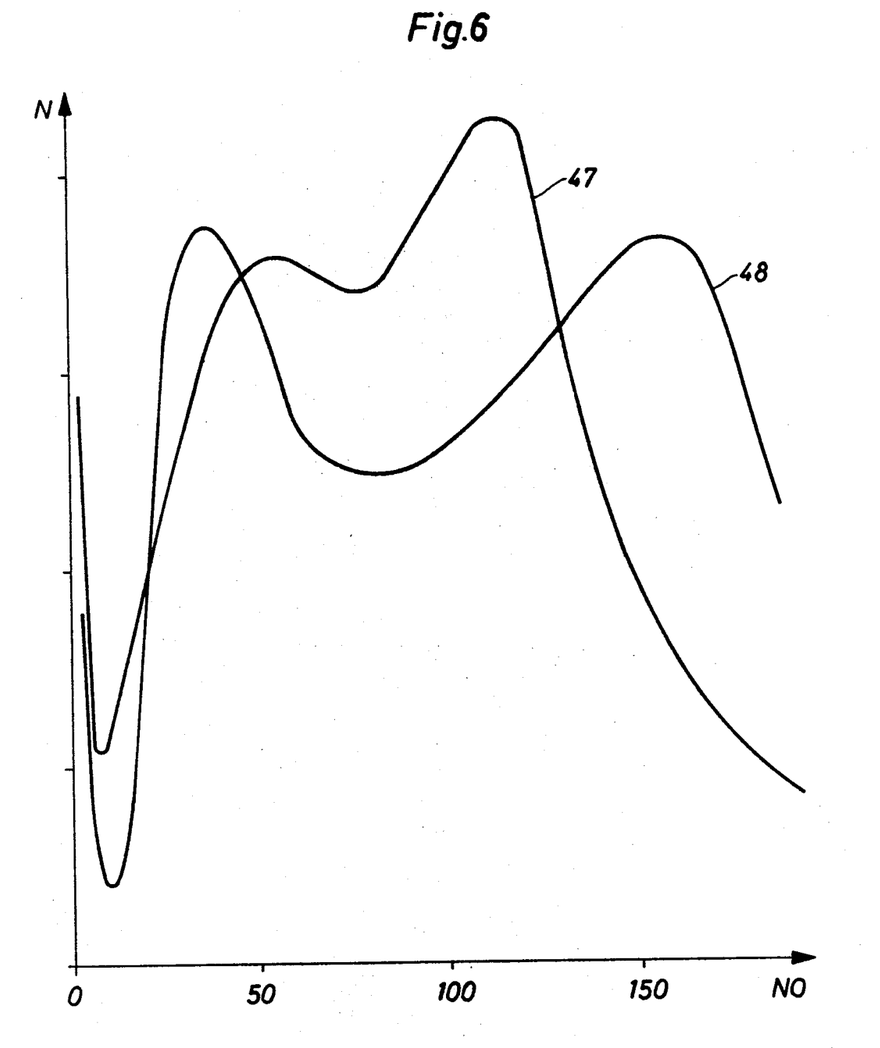
FIG. 6 is a diagram similar to that of FIG. 4 showing the measuring result for a mixed population of tetrahymena pyriformis.
Figure 7:
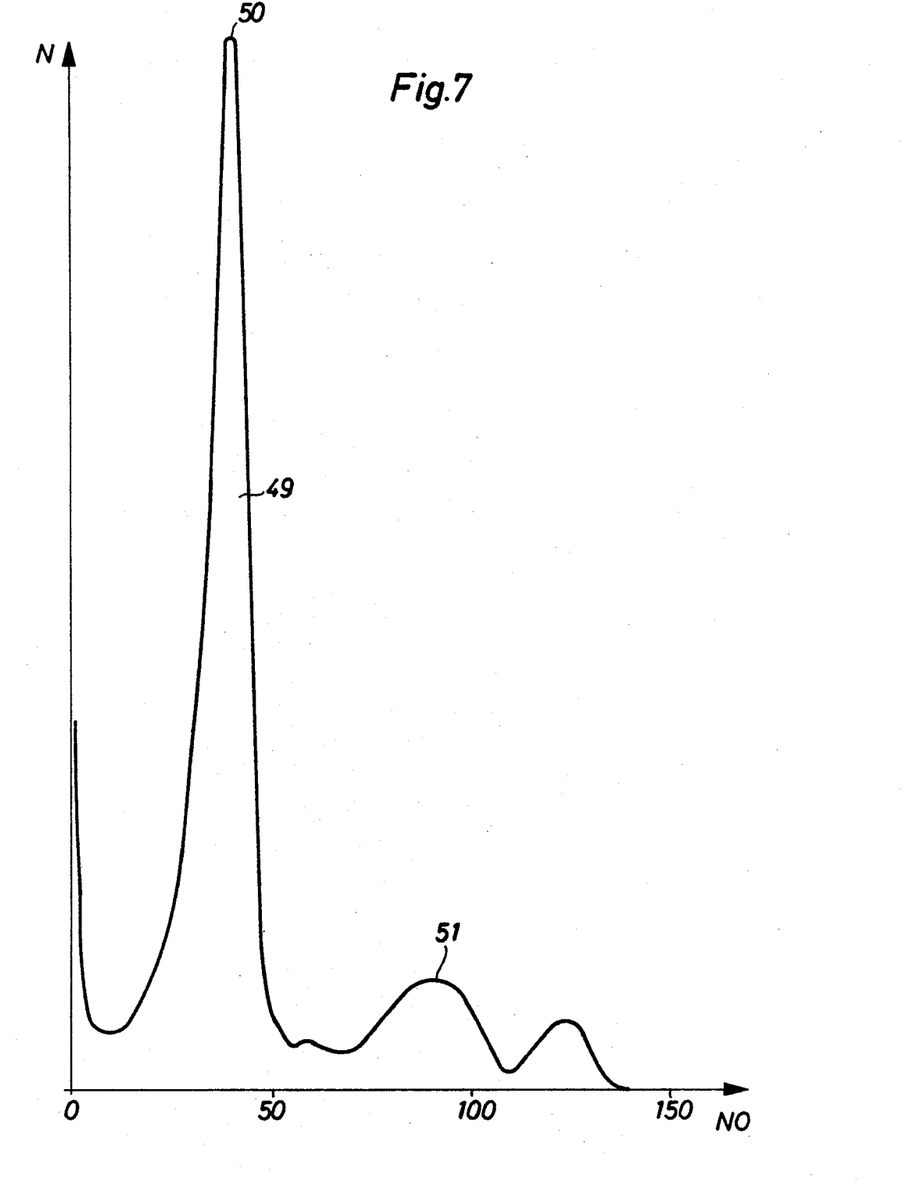
FIG. 7 is a diagram similar to that of FIG. 4 showing the measuring result for blood cells.

A relation between the information obtained from the particle size measurement and a combined information from the integral of the absorption pulses is shown in FIG. 6. Here, again, the pulse number, N, is plotted over the channel number, NO. As already noted a higher protein content in the cells or particles, respectively, leads to higher absorption values of the colored cells or particles, respectively. A mixture of two different cell populations which are difficult to sort to permit measurement of their cell lengths can easily be separated if the distribution of the integral values of the absorption pulses is considered. Curve 47 shows the distribution of the pulse widths and curve 48 the distribution of the pulse integral. As can be noted, there are always two maxima.

The system according to the invention can be used for routine checks on the size distribution of blood particles in either fresh blood or preserved blood. In this field of use it is not an advantage to color the blood cells because this may lead to agglutination of the blood cells and thus influence the size distribution. Such distribution is shown by curve 49 of FIG. 7. The first two maxima 50 and 51 relate to particle sizes of 7μ and 15μ, respectively.

It will be understood that the above description of the present invention is susceptible to various modifications, changes and adaptations, and the same are intended to be comprehended within the meaning and range of equivalents of the appended claims.

What is claimed is:

1. In apparatus for counting and measuring the major dimension of particles of nonspherical shape and including a laser for producing a laser beam and a laser radiation detector, the improvement wherein: said apparatus comprises a flow nozzle having a tapered outlet end which terminates in a capillary nozzle, means delivering a stream of such particles to said flow nozzle, means delivering a fluid into said flow nozzle upstream of said outlet end to form a first entraining stream which entrains the stream of particles and hydrodynamically focusses the particle stream into a thin stream in the first entraining stream, with the major axes of the particles aligned with the axis of the thin stream in said capillary nozzle, the hydrodynamically focussed stream being directed from said capillary nozzle to intersect the laser beam; a jacket pipe disposed around said flow nozzle and providing a second entraining stream for the entrained stream of particles leaving said capillary nozzle, and means giving the laser beam a diameter which, at the point of intersection with the particle stream, is no greater than the width of the particles; and said detector is disposed to receive the laser radiation transmitted by the particles as they pass through the laser beam.

2. An arrangement as defined in claim 1 wherein said jacket pipe comprises, in the region of the outlet end of said flow nozzle, two mutually parallel planar surfaces each provided with an aperture; and two transparent, planar discs each closing a respective aperture and disposed to permit passage of the laser beam.

3. An arrangement as defined in claim 1 wherein said flow nozzle is fastened to said jacket pipe, and said jacket pipe is provided with a common outlet arranged to be in communication with a low pressure region and positioned for withdrawing the entraining stream and the stream of particles from the interior of said jacket pipe.

4. An arrangement as defined in claim 3 wherein said jacket pipe is further provided with an inlet for a fluid providing the entraining stream.

5. An arrangement as defined in claim 3 further comprising means for delivering a fluid into said nozzle to provide a preliminary entraining stream for the stream of particles.

6. An arrangement as defined in claim 1 wherein said means bring the laser beam to a focus substantially at the point of intersection with the particle stream.

7. An arrangement as defined in claim 2 wherein the axis of said laser beam is substantially perpendicular to the planes of said discs.

* * * * *